US009187476B2

(12) United States Patent
Abele et al.

(10) Patent No.: US 9,187,476 B2
(45) Date of Patent: Nov. 17, 2015

(54) PROCESS FOR MANUFACTURING NAPHTHYRIDINE DERIVATIVES

(71) Applicant: Actelion Pharmaceuticals Ltd., Allschwil (CH)

(72) Inventors: Stefan Abele, Allschwil (CH); Hans Meier, Kaiseraugst (CH); Gunther Schmidt, Allschwil (CH); Heinz Steiner, Kaiseraugst (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 14/397,421

(22) PCT Filed: Apr. 26, 2013

(86) PCT No.: PCT/IB2013/053306
§ 371 (c)(1),
(2) Date: Oct. 27, 2014

(87) PCT Pub. No.: WO2013/160875
PCT Pub. Date: Oct. 31, 2013

(65) Prior Publication Data
US 2015/0087840 A1 Mar. 26, 2015

(30) Foreign Application Priority Data

Apr. 27, 2012 (EP) ..................................... 12002989

(51) Int. Cl.
*C07D 471/04* (2006.01)
(52) U.S. Cl.
CPC .................................. *C07D 471/04* (2013.01)
(58) Field of Classification Search
CPC ..................................................... C07D 471/04
USPC ........................................................ 546/122
See application file for complete search history.

(56) References Cited

U.S. PATENT DOCUMENTS

| | | | |
|---|---|---|---|
| 8,211,890 B2 | 7/2012 | Hubschwerlen et al. | |
| 8,927,542 B2 * | 1/2015 | Gaucher et al. | 514/230.5 |
| 2006/0041123 A1 * | 2/2006 | Axten et al. | 544/48 |
| 2007/0161627 A1 * | 7/2007 | Miller et al. | 514/218 |
| 2007/0244103 A1 * | 10/2007 | Pierau et al. | 514/227.8 |
| 2009/0131444 A1 * | 5/2009 | Reck et al. | 514/248 |
| 2010/0087424 A1 * | 4/2010 | Brown et al. | 514/224.2 |
| 2010/0256124 A1 * | 10/2010 | Davies et al. | 514/224.2 |
| 2015/0025244 A1 * | 1/2015 | Abele et al. | 546/122 |
| 2015/0057293 A1 * | 2/2015 | Angibaud et al. | 514/256 |

FOREIGN PATENT DOCUMENTS

| | | | |
|---|---|---|---|
| WO | 02/08224 | | 1/2002 |
| WO | 2004/058144 | | 7/2004 |
| WO | 2006/081178 | | 8/2006 |
| WO | 2006/081179 | | 8/2006 |
| WO | 2006/081182 | | 8/2006 |
| WO | 2006/081264 | | 8/2006 |
| WO | 2006/081289 | | 8/2006 |
| WO | 2006/125974 | | 11/2006 |
| WO | 2007016610 | * | 2/2007 |
| WO | 2008/009700 | | 1/2008 |
| WO | 2009090222 | * | 7/2009 |
| WO | 2010/067332 | | 6/2010 |
| WO | 2010/081874 | | 7/2010 |
| WO | 2013/118086 | | 8/2013 |

OTHER PUBLICATIONS

Chambers, R. et al., "Elemental Flourine. Part 10.1 Selective Fluorination of Pyridine, Quinoline and Quinoxaline Derivatives with Flourine—Iodine Mixtures," J. Chem. Soc. Perkin Trans. 1 (1999), pp. 803-810.
Chambers, R. et al., "Selective Direct Fluorination of Quinoline Derivatives," J. Fluorine Chemistry (2002), vol. 117, pp. 99-101.
Chirakal R. et al., "Synthesis of 2- and 3-Fluorotyrosine with Dilute Fluorine Gas," J. Fluorine Chemistry (1987), vol. 37, pp. 267-278.
Miles, T. et al., "Novel Amino-Piperidines as Potent Antibacterials Targeting Bacterial Type IIA Topoisomerases," Bioorg. Med. Chem. Lett (2011), vol. 21, pp. 7489-7495.
Misaki, S., "Direct Fluorination of Phenol and Cresols," J. Fluorine Chemistry (1981), vol. 17, pp. 159-171.
Misaki, S., "Direct Fluorination of Aryl Oxygen Compounds," J. Fluorine Chemistry (1982), vol. 21, pp. 191-199.
Stavber, S. et al., "Caesium Fluoroxysulphate as a Mild Fluorinating Agent for the Fluorination of Alkoxy-Substituted Benzene and Naphthalene Derivatives" J. Chem. Soc., Chem. Commun. (1981), vol. 4, p. 148.
Umemoto, T. et al., "Power and Structure-Variable Fluorinating Agents. The N-Fluoropyridinium Salt System," J. Am. Chem. Soc. (1990), vol. 112, pp. 8563-8575.
Umemoto, T. et al., "N-Fluoropyridinium Triflate and Its Derivatives: Useful Fluorinating Agents," Tetrahedron Lett. (1986), vol. 27, pp. 4465-4468.
Van Der Puy, M., "Direct Fluorination of Substituted Pyridines," Tetrahedron Lett. (1987), vol. 28, pp. 255-258.

* cited by examiner

*Primary Examiner* — Niloofar Rahmani
(74) *Attorney, Agent, or Firm* — Hunton & Williams LLP

(57) ABSTRACT

The invention relates to a new process suitable for manufacturing the compounds of formula I (I) wherein W is H, Br, Cl or methyl, which are synthetic intermediates useful in the preparation of antibiotic compounds.

15 Claims, No Drawings

PROCESS FOR MANUFACTURING NAPHTHYRIDINE DERIVATIVES

CROSS-REFERENCE TO RELATED APPLICATIONS

This application is the U.S. National Phase of International Patent Application No. PCT/IB2013/053306, filed Apr. 26, 2013, which claims the benefit of priority to European Patent Application No. EP 12002989.7, filed Apr. 27, 2012, the contents of each are hereby incorporated by reference in their entireties.

The present invention relates to a new process for manufacturing certain known naphthyridine derivatives that are useful intermediates in the preparation of antibiotic compounds, namely the compounds corresponding to formula I-3

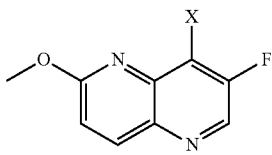

wherein X is Br or Cl.

The compound of formula I-3 wherein X is Br (hereafter referred to as "compound of formula I-3a") has been disclosed in WO 2004058144 (Example 53, intermediate 53(g)). This compound can notably be used in the preparation of antibiotic compounds such as those disclosed in WO 2004058144, WO 200681178, WO 200681179, WO 200681182, WO 200681264, WO 200681289 or T. J. Miles et al., *Bioorg. Med. Chem. Lett.* (2011), 21, 7489-7495. The compound of formula I-3 wherein X is Cl (hereafter referred to as "compound of formula I-3b") is also known as synthetic intermediate in the preparation of antibiotic compounds (see WO 2006125974, preparation of intermediate 47).

The compound of formula I-3 can be used for obtaining further useful intermediates in the preparation of antibiotic compounds, such as the compound of formula I-4

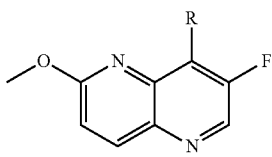

wherein R is H or methyl (see WO 2008009700 or WO 2010067332).

The known methods for preparing the compound of formula I-3 are however not most appropriate for large manufacturing, notably because of synthetic routes involving quite many steps, and/or the use of expensive reagents or reaction conditions, and/or moderate yields (see e.g. WO 2004058144 or T. J. Miles et al., *Bioorg. Med. Chem. Lett.* (2011), 21, 7489-7495).

An unexpectedly short, efficient and selective manufacturing route to obtain the compound of formula I-3 has now been found, which relies on the direct and selective conversion of the compound of formula I-1

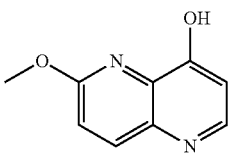

into a compound of formula I-2

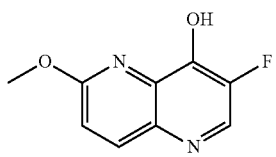

using fluorine gas ($F_2$). The compound of formula I-2 can then be converted into the desired compound of formula I-3 using methods well known to one skilled in the art.

Ortho-fluorination of 4-hydroxy pyridines with elemental fluorine gas ($F_2$) has not been described before.

Several methods have been disclosed for the electrophilic ortho fluorination of phenol derivatives. These methods rely for example on:

the use of cesium fluoroxy sulfate (S. Stavber and M. Zupan, *J. Chem. Soc., Chem. Commun.* (1981), 4, 148);

the use of N-fluorotrimethylpyridinium triflate (T. Umemoto et al., *Tetrahedron Lett.* (1986), 27, 4465-4468);

the use of 1-fluoro-3,5-dichloropyridinium trifluoromethanesulfonate (T. Umemoto et al., *J. Am. Chem. Soc.* (1990), 112, 8563-8575); or the use of elemental fluorine gas (S. Misaki, *J. Fluorine Chemistry* (1981), 17, 159-172; or S. Misaki, *J. Fluorine Chemistry* (1982), 21, 191-199; R. Chirakal et al., *J. Fluorine Chemistry* (1987), 37, 267-278).

The use of elemental fluorine gas to perform the fluorination of pyridine or quinoline derivatives has also been tried, but is well known to lead to mixtures of regioisomers (M. Van der Puy, *Tetrahedron Lett.* (1987), 28, 255-258; R. D. Chambers et al., *J. Chem. Soc., Perkin Trans.* 1 (1999), 803-810; R. D. Chambers et al., *J. Fluorine Chemistry* (2002), 117, 99-101).

It has however been unexpectedly found that reacting the compound of formula I-1 with fluorine gas under particular conditions selectively leads to the compound of formula I-2 with an excellent yield, whereas the reaction of the compound of formula I-1 with fluorine gas does not work when using the conditions described in the prior art for certain quinoline derivatives by R. D. Chambers et al. in *J. Fluorine Chemistry* (2002), 117, 99-101 (reaction with fluorine in concentrated sulfuric acid at a temperature of 0 to 5° C.). This unexpected finding opens an easy preparation route for obtaining the useful compound of formula I-3.

Various embodiments of the invention are presented hereafter:

1) The invention firstly relates to a process for manufacturing the compound of formula I-2

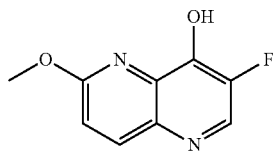

said process comprising the reaction of the compound of formula I-1

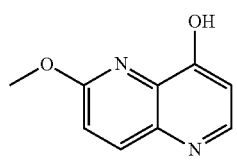

with fluorine gas in the presence of sulfuric acid at a temperature from 20 to 100° C.
2) Preferably, the reaction of the process of embodiment 1) will be performed at a temperature from 40 to 95° C.
3) More preferably, the reaction of the process of embodiment 1) will be performed at a temperature from 65 to 90° C. (and in particular at a temperature of about 80° C.).
4) Preferably, the reaction of the process of embodiments 1) to 3) will be performed in sulfuric acid having a concentration of at least 60% in weight.
5) More preferably, the reaction of the process of embodiments 1) to 3) will be performed in sulfuric acid having a concentration of at least 95% in weight (and notably a concentration of at least 98% in weight).
6) According to a preferred variant, the reaction of the process of embodiments 1) to 5) will be performed using fluorine that has gone through a frit filter.
7) Preferably, the frit filter used in the process according to embodiment 6) will have a pore size ranging from 5 to 50 μm.
8) More preferably, the frit filter used in the process according to embodiment 6) will have a pore size ranging from 10 to 25 μm (and notably a pore size of about 20 μm).
9) Preferably, the fluorine gas used in the process according to any of embodiments 1) to 8) will be provided in the form of a gaseous mixture of fluorine with an inert gas or inert gas mixture.
10) More preferably, the fluorine gas used in the process according to any of embodiments 1) to 8) will be provided in the form of a gaseous mixture of fluorine gas with nitrogen.
11) Preferably, the concentration of fluorine gas in the gaseous mixture of fluorine gas with an inert gas or inert gas mixture used in the process according to embodiment 9) or 10) will range from 0.5 to 50% in volume compared to the total volume of the gaseous mixture (and in particular from 1 to 20% in volume compared to the total volume of the gaseous mixture).
12) More preferably, the concentration of fluorine gas in the gaseous mixture of fluorine gas with an inert gas or inert gas mixture used in the process according to embodiment 9) or 10) will range from 5 to 15% in volume compared to the total volume of the gaseous mixture (and will notably amount to about 10% in volume compared to the total volume of the gaseous mixture).

13) In a particularly preferred sub-embodiment of the process according to any of embodiments 1) to 8), the fluorine gas used in the process according to any of embodiments 1) to 8) will be provided in the form of a gaseous mixture of fluorine gas with nitrogen, whereby the concentration of fluorine gas in said gaseous mixture will range from 5 to 15% in volume compared to the total volume of the gaseous mixture (and will notably amount to about 10% in volume compared to the total volume of the gaseous mixture).
14) Besides, the reaction of the process of embodiments 1) to 13) will preferably be performed in sulfuric acid with a concentration of compound of formula I-2 ranging from 0.01 to 3 moles of compound of formula I-2 per liter of sulfuric acid, and notably from 0.01 to 1 mole of compound of formula I-2 per liter of sulfuric acid.
15) In particular, the reaction of the process of embodiment 14) will be performed using a concentration of compound of formula I-2 ranging from 0.2 to 1 mole of formula I-2 per liter of sulfuric acid (especially using a concentration of about 0.6 mole of compound of formula I-2 per liter of sulfuric acid).
16) The invention will furthermore relate to the use of a process according to embodiments 1) to 15) in a method for manufacturing the compound of formula I-3

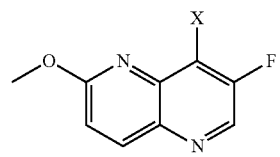

wherein X is Br or Cl.
17) According to a variant of embodiment 16), X will be Br.
18) According to the other variant of embodiment 16), X will be Cl.
19) The invention will furthermore relate to a process for manufacturing the compound of formula I-3

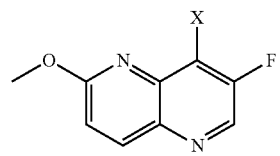

wherein X is Br or Cl, said process comprising the following steps:
  a) performing the process according to one of embodiments 1) to 15); and
  b) reacting the compound of formula I-2 obtained at step a) with tribromophosphine in a polar aprotic solvent or a polar aprotic mixture of solvents, or reacting the compound of formula I-2 obtained at step a) with phosphoryl trichloride optionally in a polar aprotic solvent or a polar aprotic mixture of solvents, thus obtaining the compound of formula I-3.
20) Preferably, the process of step a) of the process according to embodiment 19) will be performed at a temperature from 65° C. to 90° C. using sulfuric acid having a concentration of at least 95% in weight.
21) More preferably, the process of step a) of the process according to embodiment 19) will be performed at a temperature of about 80° C. using sulfuric acid having a concentration of at least 98% in weight.

22) According to one variant of embodiments 19) to 21), the compound of formula I-2 obtained at step a) will be reacted with tribromophosphine and the compound of formula I-3a will be obtained.
23) Preferably, the solvent or a mixture of solvents of step b) of the process according to embodiment 22) will comprise (and notably consist in) DMF, dimethyl acetamide, NMP, toluene, DCM or a mixture of two or more of the latter; in particular, the solvent or a mixture of solvents of step b) of the process according to embodiment 22) will comprise (and notably consist in) DMF.
24) Preferably, the process according to embodiment 22) or 23) will be such that the reaction of step b) is performed at a temperature between 50° C. and the reflux temperature of the reaction mixture (and in particular at a temperature between 65° C. and the reflux temperature of the reaction mixture).
25) Step b) of the process according to any of embodiments 22) to 24) will preferably be performed using from 1 to 1.2 equivalents of tribromophosphine per equivalent of compound of formula I-2, and notably using from 1.05 to 1.15 equivalents of tribromophosphine per equivalent of compound of formula I-2.
26) Preferably, the reaction of step b) of the process according to one of embodiments 22) to 25) will be performed in a solvent or a mixture of solvents that has a boiling point of at least 80° C. (and preferably a boiling point of at least 100° C.).
27) According to the other variant of embodiments 19) to 21), the compound of formula I-2 obtained at step a) will be reacted with phosphoryl trichloride and the compound of formula I-3b will be obtained.
28) Preferably, the process according to embodiment 27) will be such that the reaction of its step b) is performed at a temperature between 0 and 30° C. (and in particular at a temperature between 4° C. and 28° C.).
29) Step b) of the process according to embodiment 27) or 28) will preferably be performed using from 1.5 to 2.5 equivalents of phosphoryl trichloride per equivalent of compound of formula I-2, and notably using from 1.8 to 2.2 equivalents of phosphoryl trichloride per equivalent of compound of formula I-2.
30) Preferably, the solvent or a mixture of solvents of step b) of the process according to one of embodiments 27) to 29), when present, will comprise (and notably consist in) DMF, dimethyl acetamide, NMP, toluene, DCM or a mixture of two or more of the latter; in particular, the solvent or a mixture of solvents of step b) of the process according to one of embodiments 27) to 29), when present, will comprise (and notably consist in) DMF.
31) A further embodiment of this invention relates to the use of a process according to embodiments 1) to 15) in a method for manufacturing the compound of formula I-4

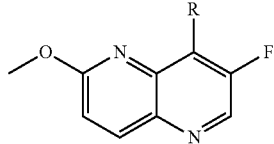

wherein R is H or methyl.

The preparation of the compound of formula I-4 from the compound of formula I-2 can be performed according to standard methods known to one skilled in the art. For example, the process according to embodiment 27) can be used to obtain the compound of formula I-3b; the latter can then be converted into the compound of formula I-4 wherein R is H (see e.g. WO 2008009700) or into the compound of formula I-4 wherein R is methyl (see e.g. WO 2010067332).
32) According to a variant of embodiment 31), R will be H.
33) According to the other variant of embodiment 31), R will be methyl.
34) Yet a further embodiment of this invention relates to the use of a process according to one of embodiments 27) to 30) in a method for manufacturing the compound of formula I-4

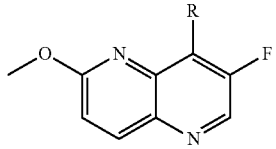

wherein R is H or methyl.
35) According to a variant of embodiment 34), R will be H.
36) According to the other variant of embodiment 34), R will be methyl.

This invention thus notably relates to the manufacturing processes and uses as defined in one of embodiments 1), 16), 19), 31) and 34) or to these manufacturing processes and uses further limited under consideration of their respective dependencies by the characteristics of any one of embodiments 2) to 15), 17), 18), 20) to 30), 32), 33), 35) and 36). In particular, based on the dependencies of the different embodiments as disclosed hereinabove, the following manufacturing process and use embodiments are thus possible and intended and herewith specifically disclosed in individualized form:

1, 2+1, 3+1, 4+1, 4+2+1, 4+3+1, 5+1, 5+2+1, 5+3+1, 6+1, 6+2+1, 6+3+1, 6+4+1, 6+4+2+1, 6+4+3+1, 6+5+1, 6+5+2+1, 6+5+3+1, 7+6+1, 7+6+2+1, 7+6+3+1, 7+6+4+1, 7+6+4+2+1, 7+6+4+3+1, 7+6+5+1, 7+6+5+2+1, 7+6+5+3+1, 8+6+1, 8+6+2+1, 8+6+3+1, 8+6+4+1, 8+6+4+2+1, 8+6+4+3+1, 8+6+5+1, 8+6+5+2+1, 8+6+5+3+1, 9+1, 9+3+1, 9+5+1, 9+5+2+1, 9+5+3+1, 9+6+1, 9+6+2+1, 9+6+3+1, 9+6+4+1, 9+6+4+2+1, 9+6+4+3+1, 9+6+5+1, 9+6+5+2+1, 9+6+5+3+1, 10+1, 10+3+1, 10+5+1, 10+5+2+1, 10+5+3+1, 10+6+1, 10+6+2+1, 10+6+3+1, 10+6+4+1, 10+6+4+2+1, 10+6+4+3+1, 10+6+5+1, 10+6+5+2+1, 10+6+5+3+1, 11+9+1, 11+9+3+1, 11+9+5+1, 11+9+5+2+1, 11+9+5+3+1, 11+9+6+1, 11+9+6+2+1, 11+9+6+3+1, 11+9+6+4+1, 11+9+6+4+2+1, 11+9+6+4+3+1, 11+9+6+5+1, 11+9+6+5+2+1, 11+9+6+5+3+1, 11+10+1, 11+10+3+1, 11+10+5+1, 11+10+5+2+1, 11+10+5+3+1, 11+10+6+1, 11+10+6+2+1, 11+10+6+3+1, 11+10+6+4+1, 11+10+6+4+2+1, 11+10+6+4+3+1, 11+10+6+5+1, 11+10+6+5+2+1, 11+10+6+5+3+1, 12+9+1, 12+9+3+1, 12+9+5+1, 12+9+5+2+1, 12+9+5+3+1, 12+9+6+1, 12+9+6+2+1, 12+9+6+3+1, 12+9+6+4+1, 12+9+6+4+2+1, 12+9+6+4+3+1, 12+9+6+5+1, 12+9+6+5+2+1, 12+9+6+5+3+1, 12+10+1, 12+10+3+1, 12+10+5+1, 12+10+5+2+1, 12+10+5+3+1, 12+10+6+1, 12+10+6+2+1, 12+10+6+3+1, 12+10+6+4+1, 12+10+6+4+2+1, 12+10+6+4+3+1, 12+10+6+5+1, 12+10+6+5+2+1, 12+10+6+5+3+1, 13+1, 13+3+1, 13+5+1, 13+5+2+1, 13+5+3+1, 13+6+1, 13+6+2+1, 13+6+3+1, 13+6+4+1, 13+6+4+2+1, 13+6+4+3+1, 13+6+5+1, 13+6+5+2+1, 13+6+5+3+1, 14+1, 14+3+1, 14+5+1, 14+5+2+1, 14+5+3+1, 14+6+1, 14+6+2+1, 14+6+3+1, 14+6+4+1, 14+6+4+2+1, 14+6+4+3+1, 14+6+5+1, 14+6+5+2+1, 14+6+5+3+1, 15+14+1, 15+14+3+1, 15+14+5+1, 15+14+5+2+1, 15+14+5+3+1, 15+14+6+1, 15+14+6+2+1, 15+14+6+3+1, 15+14+6+4+1, 15+14+6+4+2+1, 15+14+6+4+3+1, 15+14+6+5+1, 15+14+6+5+2+1, 15+14+6+5+3+1, 16+1, 16+3+1,

16+5+1, 16+5+2+1, 16+5+3+1, 16+6+1, 16+6+2+1, 16+6+3+1, 16+6+4+1, 16+6+4+2+1, 16+6+4+3+1, 16+6+5+1, ≠+6+5+2+1, 16+6+5+3+1, 17+16+1, 17+16+3+1, 17+16+5+1, 17+16+5+2+1, 17+16+5+3+1, 17+16+6+1, 17+16+6+2+1, 17+16+6+3+1, 17+16+6+4+1, 17+16+6+4+2+1, 17+16+6+4+3+1, 17+16+6+5+1, 17+16+6+5+2°1, 17+16+6+5+3+1, 18+16+1, 18+16+3+1, 18+16+5+1, 18+16+5+2+1, 18+16+5+3+1, 18+16+6+1, 18+16+6+2+1, 18+16+6+3+1, 18+16+6+4+1, 18+16+6+4+2+1, 18+16+6+4+3+1, 18+16+6+5+1, 18+16+6+5+2+1, 18+16+6+5+3+1, 19+1, 19+3+1, 19+5+1, 19+5+2+1, 19+5+3+1, 19+6+1, 19+6+2+1, 19+6+3+1, 19+6+4+1, 19+6+4+2+1, 19+6+4+3+1, 19+6+5+1, 19+6+5+2+1, 19+6+5+3+1, 20+19+1, 20+19+3+1, 20+19+5+1, 20+19+5+2+1, 20+19+5+3+1, 20+19+6+1, 20+19+6+2+1, 20+19+6+3+1, 20+19+6+4+1, 20+19+6+4+2+1, 20+19+6+4+3+1, 20+19+6+5+1, 20+19+6+5+2+1, 20+19+6+5+3+1, 21+19+1, 21+19+3+1, 21+19+5+1, 21+19+5+2+1, 21+19+5+3+1, 21+19+6+1, 21+19+6+2+1, 21+19+6+3+1, 21+19+6+4+1, 21+19+6+4+2+1, 21+19+6+4+3+1, 21+19+6+5+1, 21+19+6+5+2+1, 21+19+6+5+3+1, 22+19+1, 22+19+3+1, 22+19+5+1, 22+19+5+2+1, 22+19+5+3+1, 22+19+6+1, 22+19+6+2+1, 22+19+6+3+1, 22+19+6+4+1, 22+19+6+4+2+1, 22+19+6+4+3+1, 22+19+6+5+1, 22+19+6+5+2+1, 22+19+6+5+3+1, 22+20+19+1, 22+20+19+3+1, 22+20+19+5+1, 22+20+19+5+2+1, 22+20+19+5+3+1, 22+20+19+6+1, 22+20+19+6+2+1, 22+20+19+6+3+1, 22+20+19+6+4+1, 22+20+19+6+4+2+1, 22+20+19+6+4+3+1, 22+20+19+6+5+1, 22+20+19+6+5+2+1, 22+20+19+6+5+3+1, 22+21+19+1, 22+21+19+3+1, 22+21+19+5+1, 22+21+19+5+2+1, 22+21+19+5+3+1, 22+21+19+6+1, 22+21+19+6+2+1, 22+21+19+6+3+1, 22+21+19+6+4+1, 22+21+19+6+4+2+1, 22+21+19+6+4+3+1, 22+21+19+6+5+1, 22+21+19+6+5+2+1, 22+21+19+6+5+3+1, 23+22+19+1, 23+22+19+3+1, 23+22+19+5+1, 23+22+19+5+2+1, 23+22+19+5+3+1, 23+22+19+6+1, 23+22+19+6+2+1, 23+22+19+6+3+1, 23+22+19+6+4+1, 23+22+19+6+4+2+1, 23+22+19+6+4+3+1, 23+22+19+6+5+1, 23+22+19+6+5+2+1, 23+22+19+6+5+3+1, 23+22+20+19+1, 23+22+20+19+3+1, 23+22+20+19+5+1, 23+22+20+19+5+2+1, 23+22+20+19+5+3+1, 23+22+20+19+6+1, 23+22+20+19+6+2+1, 23+22+20+19+6+3+1, 23+22+20+19+6+4+1, 23+22+20+19+6+4+2+1, 23+22+20+19+6+4+3+1, 23+22+20+19+6+5+1, 23+22+20+19+6+5+2+1, 23+22+20+19+6+5+3+1, 23+22+21+19+1, 23+22+21+19+3+1, 23+22+21+19+5+1, 23+22+21+19+5+2+1, 23+22+21+19+5+3+1, 23+22+21+19+6+1, 23+22+21+19+6+2+1, 23+22+21+19+6+3+1, 23+22+21+19+6+4+1, 23+22+21+19+6+4+2+1, 23+22+21+19+6+4+3+1, 23+22+21+19+6+5+1, 23+22+21+19+6+5+2+1, 23+22+21+19+6+5+3+1, 24+22+19+1, 24+22+19+3+1, 24+22+19+5+1, 24+22+19+5+2+1, 24+22+19+5+3+1, 24+22+19+6+1, 24+22+19+6+2+1, 24+22+19+6+3+1, 24+22+19+6+4+1, 24+22+19+6+4+2+1, 24+22+19+6+4+3+1, 24+22+19+6+5+1, 24+22+19+6+5+2+1, 24+22+19+6+5+3+1, 24+22+20+19+1, 24+22+20+19+3+1, 24+22+20+19+5+1, 24+22+20+19+5+2+1, 24+22+20+19+5+3+1, 24+22+20+19+6+1, 24+22+20+19+6+2+1, 24+22+20+19+6+3+1, 24+22+20+19+6+4+1, 24+22+20+19+6+4+2+1, 24+22+20+19+6+4+3+1, 24+22+20+19+6+5+1, 24+22+20+19+6+5+2+1, 24+22+20+19+6+5+3+1, 24+22+21+19+1, 24+22+21+19+3+1, 24+22+21+19+5+1, 24+22+21+19+5+2+1, 24+22+21+19+5+3+1, 24+22+21+19+6+1, 24+22+21+19+6+2+1, 24+22+21+19+6+3+1, 24+22+21+19+6+4+1, 24+22+21+19+6+4+2+1, 24+22+21+19+6+4+3+1, 24+22+21+19+6+5+1, 24+22+21+19+6+5+2+1, 24+22+21+19+6+5+3+1, 24+23+22+19+1, 24+23+22+19+3+1, 24+23+22+19+5+1, 24+23+22+19+5+2+1, 24+23+22+19+5+3+1, 24+23+22+19+6+1, 24+23+22+19+6+2+1, 24+23+22+19+6+3+1, 24+23+22+19+6+4+1, 24+23+22+19+6+4+2+1, 24+23+22+19+6+4+3+1, 24+23+22+19+6+5+1, 24+23+22+19+6+5+2+1, 24+23+22+19+6+5+3+1, 24+23+22+20+19+1, 24+23+22+20+19+3+1, 24+23+22+20+19+5+1, 24+23+22+20+19+5+2+1, 24+23+22+20+19+5+3+1, 24+23+22+20+19+6+1, 24+23+22+20+19+6+2+1, 24+23+22+20+19+6+3+1, 24+23+22+20+19+6+4+1, 24+23+22+20+19+6+4+2+1, 24+23+22+20+19+6+4+3+1, 24+23+22+20+19+6+5+1, 24+23+22+20+19+6+5+2+1, 24+23+22+20+19+6+5+3+1, 24+23+22+21+19+1, 24+23+22+21+19+3+1, 24+23+22+21+19+5+1, 24+23+22+21+19+5+2+1, 24+23+22+21+19+5+3+1, 24+23+22+21+19+6+1, 24+23+22+21+19+6+2+1, 24+23+22+21+19+6+3+1, 24+23+22+21+19+6+4+1, 24+23+22+21+19+6+4+2+1, 24+23+22+21+19+6+4+3+1, 24+23+22+21+19+6+5+1, 24+23+22+21+19+6+5+2+1, 24+23+22+21+19+6+5+3+1, 25+22+19+1, 25+22+19+3+1, 25+22+19+5+1, 25+22+19+5+2+1, 25+22+19+5+3+1, 25+22+19+6+1, 25+22+19+6+2+1, 25+22+19+6+3+1, 25+22+19+6+4+1, 25+22+19+6+4+2+1, 25+22+19+6+4+3+1, 25+22+19+6+5+1, 25+22+19+6+5+2+1, 25+22+19+6+5+3+1, 25+22+20+19+1, 25+22+20+19+3+1, 25+22+20+19+5+1, 25+22+20+19+5+2+1, 25+22+20+19+5+3+1, 25+22+20+19+6+1, 25+22+20+19+6+2+1, 25+22+20+19+6+3+1, 25+22+20+19+6+4+1, 25+22+20+19+6+4+2+1, 25+22+20+19+6+4+3+1, 25+22+20+19+6+5+1, 25+22+20+19+6+5+2+1, 25+22+20+19+6+5+3+1, 25+22+21+19+1, 25+22+21+19+3+1, 25+22+21+19+5+1, 25+22+21+19+5+2+1, 25+22+21+19+5+3+1, 25+22+21+19+6+1, 25+22+21+19+6+2+1, 25+22+21+19+6+3+1, 25+22+21+19+6+4+1, 25+22+21+19+6+4+2+1, 25+22+21+19+6+4+3+1, 25+22+21+19+6+5+1, 25+22+21+19+6+5+2+1, 25+22+21+19+6+5+3+1, 25+23+22+19+1, 25+23+22+19+3+1, 25+23+22+19+5+1, 25+23+22+19+5+2+1, 25+23+22+19+5+3+1, 25+23+22+19+6+1, 25+23+22+19+6+2+1, 25+23+22+19+6+3+1, 25+23+22+19+6+4+1, 25+23+22+19+6+4+2+1, 25+23+22+19+6+4+3+1, 25+23+22+19+6+5+1, 25+23+22+19+6+5+2+1, 25+23+22+19+6+5+3+1, 25+23+22+20+19+1, 25+23+22+20+19+3+1, 25+23+22+20+19+5+1, 25+23+22+20+19+5+2+1, 25+23+22+20+19+5+3+1, 25+23+22+20+19+6+1, 25+23+22+20+19+6+2+1, 25+23+22+20+19+6+3+1, 25+23+22+20+19+6+4+1, 25+23+22+20+19+6+4+2+1, 25+23+22+20+19+6+4+3+1, 25+23+22+20+19+6+5+1, 25+23+22+20+19+6+5+2+1, 25+23+22+20+19+6+5+3+1, 25+23+22+21+19+1, 25+23+22+21+19+3+1, 25+23+22+21+19+5+1, 25+23+22+21+19+5+2+1, 25+23+22+21+19+5+3+1, 25+23+22+21+19+6+1, 25+23+22+21+19+6+2+1, 25+23+22+21+19+6+3+1, 25+23+22+21+19+6+4+1, 25+23+22+21+19+6+4+2+1, 25+23+22+21+19+6+4+3+1, 25+23+22+21+19+6+5+1, 25+23+22+21+19+6+5+2+1, 25+23+22+21+19+6+5+3+1, 25+24+22+19+1, 25+24+22+19+3+1, 25+24+22+19+5+1, 25+24+22+19+5+2+1, 25+24+22+19+5+3+1, 25+24+22+19+6+1, 25+24+22+19+6+2+1, 25+24+22+19+6+3+1, 25+24+22+19+6+4+1, 25+24+22+19+6+4+2+1, 25+24+22+19+6+4+3+1, 25+24+22+19+6+5+1, 25+24+22+19+6+5+2+1, 25+24+22+19+6+5+3+1, 25+24+22+20+19+1, 25+24+22+20+19+3+1, 25+24+22+20+19+5+1, 25+24+22+20+19+5+2+1, 25+24+22+20+19+5+3+1, 25+24+22+20+19+6+1, 25+24+22+20+19+6+2+1, 25+24+22+20+19+6+3+1, 25+24+22+20+19+6+4+1, 25+24+22+20+19+6+4+2+1, 25+24+22+20+19+6+4+3+1, 25+24+22+20+19+6+5+1,

25+24+22+20+19+6+5+2+1, 25+24+22+20+19+6+5+3+1, 25+24+22+21+19+1, 25+24+22+21+19+3+1, 25+24+22+21+19+5+1, 25+24+22+21+19+5+2+1, 25+24+22+21+19+5+3+1, 25+24+22+21+19+6+1, 25+24+22+21+19+6+2+1, 25+24+22+21+19+6+3+1, 25+24+22+21+19+6+4+1, 25+24+22+21+19+6+4+2+1, 25+24+22+21+19+6+4+3+1, 25+24+22+21+19+6+5+1, 25+24+22+21+19+6+5+2+1, 25+24+22+21+19+6+5+3+1, 25+24+23+22+19+1, 25+24+23+22+19+3+1, 25+24+23+22+19+5+1, 25+24+23+22+19+5+2+1, 25+24+23+22+19+5+3+1, 25+24+23+22+19+6+4+1, 25+24+23+22+19+6+2+1, 25+24+23+22+19+6+3+1, 25+24+23+22+19+6+4+1, 25+24+23+22+19+6+4+2+1, 25+24+23+22+19+6+4+3+1, 25+24+23+22+19+6+5+1, 25+24+23+22+19+6+5+2+1, 25+24+23+22+19+6+5+3+1, 25+24+23+22+20+19+1, 25+24+23+22+20+19+3+1, 25+24+23+22+20+19+5+1, 25+24+23+22+20+19+5+2+1, 25+24+23+22+20+19+5+3+1, 25+24+23+22+20+19+6+1, 25+24+23+22+20+19+6+2+1, 25+24+23+22+20+19+6+3+1, 25+24+23+22+20+19+6+4+1, 25+24+23+22+20+19+6+4+2+1, 25+24+23+22+20+19+6+4+3+1, 25+24+23+22+20+19+6+5+1, 25+24+23+22+20+19+6+5+2+1, 25+24+23+22+20+19+6+5+3+1, 25+24+23+22+21+19+1, 25+24+23+22+21+19+3+1, 25+24+23+22+21+19+5+1, 25+24+23+22+21+19+5+2+1, 25+24+23+22+21+19+5+3+1, 25+24+23+22+21+19+6+1, 25+24+23+22+21+19+6+2+1, 25+24+23+22+21+19+6+3+1, 25+24+23+22+21+19+6+4+1, 25+24+23+22+21+19+6+4+2+1, 25+24+23+22+21+19+6+4+3+1, 25+24+23+22+21+19+6+5+1, 25+24+23+22+21+19+6+5+2+1, 25+24+23+22+21+19+6+5+3+1, 26+22+19+1, 26+22+19+3+1, 26+22+19+5+1, 26+22+19+5+2+1, 26+22+19+5+3+1, 26+22+19+6+1, 26+22+19+6+2+1, 26+22+19+6+3+1, 26+22+19+6+4+1, 26+22+19+6+4+2+1, 26+22+19+6+4+3+1, 26+22+19+6+5+1, 26+22+19+6+5+2+1, 26+22+19+6+5+3+1, 26+22+20+19+1, 26+22+20+19+3+1, 26+22+20+19+5+1, 26+22+20+19+5+2+1, 26+22+20+19+5+3+1, 26+22+20+19+6+1, 26+22+20+19+6+2+1, 26+22+20+19+6+3+1, 26+22+20+19+6+4+1, 26+22+20+19+6+4+2+1, 26+22+20+19+6+4+3+1, 26+22+20+19+6+5+1, 26+22+20+19+6+5+2+1, 26+22+20+19+6+5+3+1, 26+22+21+19+1, 26+22+21+19+3+1, 26+22+21+19+5+1, 26+22+21+19+5+2+1, 26+22+21+19+5+3+1, 26+22+21+19+6+1, 26+22+21+19+6+2+1, 26+22+21+19+6+3+1, 26+22+21+19+6+4+1, 26+22+21+19+6+4+2+1, 26+22+21+19+6+4+3+1, 26+22+21+19+6+5+1, 26+22+21+19+6+5+2+1, 26+22+21+19+6+5+3+1, 26+23+22+19+1, 26+23+22+19+3+1, 26+23+22+19+5+1, 26+23+22+19+5+2+1, 26+23+22+19+5+3+1, 26+23+22+19+6+1, 26+23+22+19+6+2+1, 26+23+22+19+6+3+1, 26+23+22+19+6+4+1, 26+23+22+19+6+4+2+1, 26+23+22+19+6+4+3+1, 26+23+22+19+6+5+1, 26+23+22+19+6+5+2+1, 26+23+22+19+6+5+3+1, 26+23+22+20+19+1, 26+23+22+20+19+3+1, 26+23+22+20+19+5+1, 26+23+22+20+19+5+2+1, 26+23+22+20+19+5+3+1, 26+23+22+20+19+6+1, 26+23+22+20+19+6+2+1, 26+23+22+20+19+6+3+1, 26+23+22+20+19+6+4+1, 26+23+22+20+19+6+4+2+1, 26+23+22+20+19+6+4+3+1, 26+23+22+20+19+6+5+1, 26+23+22+20+19+6+5+2+1, 26+23+22+20+19+6+5+3+1, 26+23+22+21+19+1, 26+23+22+21+19+3+1, 26+23+22+21+19+5+1, 26+23+22+21+19+5+2+1, 26+23+22+21+19+5+3+1, 26+23+22+21+19+6+1, 26+23+22+21+19+6+2+1, 26+23+22+21+19+6+3+1, 26+23+22+21+19+6+4+1, 26+23+22+21+19+6+4+2+1, 26+23+22+21+19+6+4+3+1, 26+23+22+21+19+6+5+1, 26+23+22+21+19+6+5+2+1, 26+23+22+21+19+6+5+3+1, 26+24+22+19+1, 26+24+22+19+3+1, 26+24+22+19+5+1, 26+24+22+19+5+2+1, 26+24+22+19+5+3+1, 26+24+22+19+6+1, 26+24+22+19+6+2+1, 26+24+22+19+6+3+1, 26+24+22+19+6+4+1, 26+24+22+19+6+4+2+1, 26+24+22+19+6+4+3+1, 26+24+22+19+6+5+1, 26+24+22+19+6+5+2+1, 26+24+22+19+6+5+3+1, 26+24+22+20+19+1, 26+24+22+20+19+3+1, 26+24+22+20+19+5+1, 26+24+22+20+19+5+2+1, 26+24+22+20+19+5+3+1, 26+24+22+20+19+6+1, 26+24+22+20+19+6+2+1, 26+24+22+20+19+6+3+1, 26+24+22+20+19+6+4+1, 26+24+22+20+19+6+4+2+1, 26+24+22+20+19+6+4+3+1, 26+24+22+20+19+6+5+1, 26+24+22+20+19+6+5+2+1, 26+24+22+20+19+6+5+3+1, 26+24+22+21+19+1, 26+24+22+21+19+3+1, 26+24+22+21+19+5+1, 26+24+22+31+19+5+2+1, 26+24+22+21+19+5+3+1, 26+24+22+21+19+6+1, 26+24+22+21+19+6+2+1, 26+24+22+21+19+6+3+1, 26+24+22+21+19+6+4+1, 26+24+22+21+19+6+4+2+1, 26+24+22+21+19+6+4+3+1, 26+24+22+21+19+6+5+1, 26+24+22+21+19+6+5+2+1, 26+24+22+21+19+6+5+3+1, 26+24+23+22+19+1, 26+24+23+22+19+3+1, 26+24+23+22+19+5+1, 26+24+23+22+19+5+2+1, 26+24+23+22+19+5+3+1, 26+24+23+22+19+6+1, 26+24+23+22+19+6+2+1, 26+24+23+22+19+6+3+1, 26+24+23+22+19+6+4+1, 26+24+23+22+19+6+4+2+1, 26+24+23+22+19+6+4+3+1, 26+24+23+22+19+6+5+1, 26+24+23+22+19+6+5+2+1, 26+24+23+22+19+6+5+3+1, 26+24+23+22+20+19+1, 26+24+23+22+20+19+3+1, 26+24+23+22+20+19+5+1, 26+24+23+22+20+19+5+2+1, 26+24+23+22+20+19+5+3+1, 26+24+23+22+20+19+6+1, 26+24+23+22+20+19+6+2+1, 26+24+23+22+20+19+6+3+1, 26+24+23+22+20+19+6+4+1, 26+24+23+22+20+19+6+4+2+1, 26+24+23+22+20+19+6+4+3+1, 26+24+23+22+20+19+6+5+1, 26+24+23+22+20+19+6+5+2+1, 26+24+23+22+20+19+6+5+3+1, 26+24+23+22+21+19+1, 26+24+23+22+21+19+3+1, 26+24+23+22+21+19+5+1, 26+24+23+22+21+19+5+2+1, 26+24+23+22+21+19+5+3+1, 26+24+23+22+21+19+6+1, 26+24+23+22+21+19+6+2+1, 26+24+23+22+21+19+6+3+1, 26+24+23+22+21+19+6+4+1, 26+24+23+22+21+19+6+4+2+1, 26+24+23+22+21+19+6+4+3+1, 26+24+23+22+21+19+6+5+1, 26+24+23+22+21+19+6+5+2+1, 26+24+23+22+21+19+6+5+3+1, 26+25+22+19+1, 26+25+22+19+3+1, 26+25+22+19+5+1, 26+25+22+19+5+2+1, 26+25+22+19+5+3+1, 26+25+22+19+6+1, 26+25+22+19+6+2+1, 26+25+22+19+6+3+1, 26±25+22+19+6+4+1, 26+25+22+19+6+4+2+1, 26+25+22+19+6+4+3+1, 26+25+22+19+6+5+1, 26+25+22+19+6+5+2+1, 26+25+22+19+6+5+3+1, 26+25+22+20+19+1, 26+25+22+20+19+3+1, 26+25+22+20+19+5+1, 26+25+22+20+19+5+2+1, 26+25+22+20+19+5+3+1, 26+25+22+20+19+6+1, 26+25+22+20+19+6+2+1, 26+25+22+20+19+6+3+1, 26+25+22+20+19+6+4+1, 26+25+22+20+19+6+4+2+1, 26+25+22+20+19+6+4+3+1, 26+25+22+20+19+6+5+1, 26+25+22+20+19+6+5+2+1, 26+25+22+20+19+6+5+3+1,

26+25+22+21+19+1, 26+25+22+21+19+3+1, 26+25+22+21+19+5+1, 26+25+22+21+19+5+2+1, 26+25+22+21+19+5+3+1, 26+25+22+21+19+6+1, 26+25+22+21+19+6+2+1, 26+25+22+21+19+6+3+1, 26+25+22+21+19+6+4+1, 26+25+22+21+19+6+4+2+1, 26+25+22+21+19+6+4+3+1, 26+25+22+21+19+6+5+1, 26+25+22+21+19+6+5+2+1, 26+25+22+21+19+6+5+3+1, 26+25+23+22+19+1, 26+25+23+22+19+3+1, 26+25+23+22+19+5+1, 26+25+23+22+19+5+2+1, 26+25+23+22+19+5+3+1, 26+25+23+22+19+6+1, 26+25+23+22+19+6+2+1, 26+25+23+22+19+6+3+1, 26+25+23+22+19+6+4+1, 26+25+23+22+19+6+4+2+1, 26+25+23+22+19+6+4+3+1, 26+25+23+22+19+6+5+1, 26+25+23+22+19+6+5+2+1, 26+25+23+22+19+6+5+3+1, 26+25+23+22+20+19+1, 26+25+23+22+20+19+3+1, 26+25+23+22+20+19+5+1, 26+25+23+22+20+19+5+2+1, 26+25+23+22+20+19+5+3+1, 26+25+23+22+20+19+6+1, 26+25+23+22+20+19+6+2+1, 26+25+23+22+20+19+6+3+1. 26+25+23+22+20+19+6+4+1, 26+25+23+22+20+19+6+4+2+1, 26+25+23+22+20+19+6+4+3+1, 26+25+23+22+20+19+6+5+1, 26+25+23+22+20+19+6+5+2+1, 26+25+23+22+20+19+6+5+3+1, 26+25+23+22+21+19+1, 26+25+23+22+21+19+3+1, 26+25+23+22+21+19+5+1, 26+25+23+22+21+19+5+2+1, 26+25+23+22+21+19+5+3+1, 26+25+23+22+21+19+6+1, 26+25+23+22+21+19+6+2+1, 26+25+23+22+21+19+6+3+1, 26+25+23+22+21+19+6+4+1, 26+25+23+22+21+19+6+4+2+1, 26+25+23+22+21+19+6+4+3+1, 26+25+23+22+21+19+6+5+1, 26+25+23+22+21+19+6+5+2+1, 26+25+23+22+21+19+6+5+3+1, 26+25+24+22+19+1, 26+25+24+22+19+3+1, 26+25+24+22+19+5+1, 26+25+24+22+19+5+2+1, 26+25+24+22+19+5+3+1, 26+25+24+22+19+6+1, 26+25+24+22+19+6+2+1, 26+25+24+22+19+6+3+1, 26+25+24+22+19+6+4+1, 26+25+24+22+19+6+4+2+1, 26+25+24+22+19+6+4+3+1, 26+25+24+22+19+6+5+1, 26+25+24+22+19+6+5+2+1, 26+25+24+22+19+6+5+3+1, 26+25+24+22+20+19+1, 26+25+24+22+20+19+3+1, 26+25+24+22+20+19+5+1, 26+25+24+22+20+19+5+2+1, 26+25+24+22+20+19+5+3+1, 26+25+24+22+20+19+6+1, 26+25+24+22+20+19+6+2+1, 26+25+24+22+20+19+6+3+1, 26+25+24+22+20+19+6+4+1, 26+25+24+22+20+19+6+4+2+1, 26+25+24+22+20+19+6+4+3+1, 26+25+24+22+20+19+6+5+1, 26+25+24+22+20+19+6+5+2+1, 26+25+24+22+20+19+6+5+3+1, 26+25+24+22+21+19+1, 26+25+24+22+21+19+3+1, 26+25+24+22+21+19+5+1, 26+25+24+22+21+19+5+2+1, 26+25+24+22+21+19+5+3+1, 26+25+24+22+21+19+6+1, 26+25+24+22+21+19+6+2+1, 26+25+24+22+21+19+6+3+1, 26+25+24+22+21+19+6+4+1, 26+25+24+22+21+19+6+4+2+1, 26+25+24+22+21+19+6+4+3+1, 26+25+24+22+21+19+6+5+1, 26+25+24+22+21+19+6+5+2+1, 26+25+24+22+21+19+6+5+3+1, 26+25+24+23+22+19+1, 26+25+24+23+22+19+3+1, 26+25+24+23+22+19+5+1, 26+25+24+23+22+19+5+2+1, 26+25+24+23+22+19+5+3+1, 26+25+24+23+22+19+6+1, 26+25+24+23+22+19+6+2+1, 26+25+24+23+22+19+6+3+1, 26+25+24+23+22+19+6+4+1, 26+25+24+23+22+19+6+4+2+1, 26+25+24+23+22+19+6+4+3+1, 26+25+24+23+22+19+6+5+1, 26+25+24+23+22+19+6+5+2+1, 26+25+24+23+22+19+6+5+3+1, 26+25+24+23+22+20+19+1, 26+25+24+23+22+20+19+3+1, 26+25+24+23+22+20+19+5+1, 26+25+24+23+22+20+19+5+2+1, 26+25+24+23+22+20+19+5+3+1, 26+25+24+23+22+20+19+6+1, 26+25+24+23+22+20+19+6+2+1, 26+25+24+23+22+20+19+6+3+1, 26+25+24+23+22+20+19+6+4+1, 26+25+24+23+22+20+19+6+4+2+1, 26+25+24+23+22+20+19+6+4+3+1, 26+25+24+23+22+20+19+6+5+1, 26+25+24+23+22+20+19+6+5+2+1, 26+25+24+23+22+20+19+6+5+3+1, 26+25+24+23+22+21+19+1, 26+25+24+23+22+21+19+3+1, 26+25+24+23+22+21+19+5+1, 26+25+24+23+22+21+19+5+2+1, 26+25+24+23+22+21+19+5+3+1, 26+25+24+23+22+21+19+6+1, 26+25+24+23+22+21+19+6+2+1, 26+25+24+23+22+21+19+6+3+1, 26+25+24+23+22+21+19+6+4+1, 26+25+24+23+22+21+19+6+4+2+1, 26+25+24+23+22+21+19+6+4+3+1, 26+25+24+23+22+21+19+6+5+1, 26+25+24+23+22+21+19+6+5+2+1, 26+25+24+23+22+21+19+6+5+3+1, 27+19+1, 27+19+3+1, 27+19+5+1, 27+19+5+2+1, 27+19+5+3+1, 27+19+6+1, 27+19+6+2+1, 27+19+6+3+1, 27+19+6+4+1, 27+19+6+4+2+1, 27+19+6+4+3+1, 27+19+6+5+1, 27+19+6+5+2+1, 27+19+6+5+3+1, 27+20+19+1, 27+20+19+3+1, 27+20+19+5+1, 27+20+19+5+2+1, 27+20+19+5+3+1, 27+20+19+6+1, 27+20+19+6+2+1, 27+20+19+6+3+1, 27+20+19+6+4+1, 27+20+19+6+4+2+1, 27+20+19+6+4+3+1, 27+20+19+6+5+1, 27+20+19+6+5+2+1, 27+20+19+6+5+3+1, 27+21+19+1, 27+21+19+3+1, 27+21+19+5+1, 27+21+19+5+2+1, 27+21+19+5+3+1, 27+21+19+6+1, 27+21+19+6+2+1, 27+21+19+6+3+1, 27+21+19+6+4+1, 27+21+19+6+4+2+1, 27+21+19+6+4+3+1, 27+21+19+6+5+1, 27+21+19+6+5+2+1, 27+21+19+6+5+3+1, 28+27+19+1, 28+27+19+3+1, 28+27+19+5+1, 28+27+19+5+2+1, 28+27+19+5+3+1, 28+27+19+6+1, 28+27+19+6+2+1, 28+27+19+6+3+1, 28+27+19+6+4+1, 28+27+19+6+4+2+1, 28+27+19+6+4+3+1, 28+27+19+6+5+1, 28+27+19+6+5+2+1, 28+27+19+6+5+3+1, 28+27+20+19+1, 28+27+20+19+3+1, 28+27+20+19+5+1, 28+27+20+19+5+2+1, 28+27+20+19+5+3+1, 28+27+20+19+6+1, 28+27+20+19+6+2+1, 28+27+20+19+6+3+1, 28+27+20+19+6+4+1, 28+27+20+19+6+4+2+1, 28+27+20+19+6+4+3+1, 28+27+20+19+6+5+1, 28+27+20+19+6+5+2+1, 28+27+20+19+6+5+3+1, 28+27+21+19+1, 28+27+21+19+3+1, 28+27+21+19+5+1, 28+27+21+19+5+2+1, 28+27+21+19+5+3+1, 28+27+21+19+6+1, 28+27+21+19+6+2+1, 28+27+21+19+6+3+1, 28+27+21+19+6+4+1, 28+27+21+19+6+4+2+1, 28+27+21+19+6+4+3+1, 28+27+21+19+6+5+1, 28+27+21+19+6+5+2+1, 28+27+21+19+6+5+3+1, 29+27+19+1, 29+27+19+3+1, 29+27+19+5+1,

29+27+19+5+2+1, 29+27+19+5+3+1, 29+27+19+6+1, 29+27+19+6+2+1, 29+27+19+6+3+1, 29+27+19+6+4+1, 29+27+19+6+4+2+1, 29+27+19+6+4+3+1, 29+27+19+6+5+1, 29+27+19+6+5+2+1, 29+27+19+6+5+3+1, 29+27+20+19+1, 29+27+20+19+3+1, 29+27+20+19+5+1, 29+27+20+19+5+2+1, 29+27+20+19+5+3+1, 29+27+20+19+6+1, 29+27+20+19+6+2+1, 29+27+20+19+6+3+1, 29+27+20+19+6+4+1, 29+27+20+19+6+4+2+1, 29+27+20+19+6+4+3+1, 29+27+20+19+6+5+1, 29+27+20+19+6+5+2+1, 29+27+20+19+6+5+3+1, 29+27+21+19+1, 29+27+21+19+3+1, 29+27+21+19+5+1, 29+27+21+19+5+2+1, 29+27+21+19+5+3+1, 29+27+21+19+6+1, 29+27+21+19+6+2+1, 29+27+21+19+6+3+1, 29+27+21+19+6+4+1, 29+27+21+19+6+4+2+1, 29+27+21+19+6+4+3+1, 29+27+21+19+6+5+1, 29+27+21+19+6+5+2+1, 29+27+21+19+6+5+3+1, 29+28+27+19+1, 29+28+27+19+3+1, 29+28+27+19+5+1, 29+28+27+19+5+2+1, 29+28+27+19+5+3+1, 29+28+27+19+6+1, 29+28+27+19+6+2+1, 29+28+27+19+6+3+1, 29+28+27+19+6+4+1, 29+28+27+19+6+4+2+1, 29+28+27+19+6+4+3+1, 29+28+27+19+6+5+1, 29+28+27+19+6+5+2+1, 29+28+27+19+6+5+3+1, 29+28+27+20+19+1, 29+28+27+20+19+3+1, 29+28+27+20+19+5+1, 29+28+27+20+19+5+2+1, 29+28+27+20+19+5+3+1, 29+28+27+20+19+6+1, 29+28+27+20+19+6+2+1, 29+28+27+20+19+6+3+1, 29+28+27+20+19+6+4+1, 29+28+27+20+19+6+4+2+1, 29+28+27+20+19+6+4+3+1, 29+28+27+20+19+6+5+1, 29+28+27+20+19+6+5+2+1, 29+28+27+20+19+6+5+3+1, 29+28+27+21+19+1, 29+28+27+21+19+3+1, 29+28+27+21+19+5+1, 29+28+27+21+19+5+2+1, 29+28+27+21+19+5+3+1, 29+28+27+21+19+6+1, 29+28+27+21+19+6+2+1, 29+28+27+21+19+6+3+1, 29+28+27+21+19+6+4+1, 29+28+27+21+19+6+4+2+1, 29+28+27+21+19+6+4+3+1, 29+28+27+21+19+6+5+1, 29+28+27+21+19+6+5+2+1, 29+28+27+21+19+6+5+3+1, 30+27+19+1, 30+27+19+3+1, 30+27+19+5+1, 30+27+19+5+2+1, 30+27+19+5+3+1, 30+27+19+6+1, 30+27+19+6+1, 30+27+19+6+2+1, 30+27+19+6+3+1, 30+27+19+6+4+1, 30+27+19+6+4+2+1, 30+27+19+6+4+3+1, 30+27+19+6+5+1, 30+27+19+6+5+2+1, 30+27+19+6+5+3+1, 30+27+20+19+1, 30+27+20+19+3+1, 30+27+20+19+5+1, 30+27+20+19+5+2+1, 30+27+20+19+5+3+1, 30+27+20+19+6+1, 30+27+20+19+6+2+1, 30+27+20+19+6+3+1, 30+27+20+19+6+4+1, 30+77+20+19+6+4+2+1, 30+27+20+19+6+4+3+1, 30+27+20+19+6+5+1, 30+27+20+19+6+5+2+1, 30+27+20+19+6+5+3+1, 30+27+21+19+1, 30+27+21+19+3+1, 30+27+21+19+5+1, 30+27+21+19+5+2+1, 30+27+21+19+5+3+1, 30+27+21+19+6+1, 30+27+21+19+6+2+1, 30+27+21+19+6+3+1, 30+27+21+19+6+4+1, 30+27+21+19+6+4+2+1, 30+27+21+19+6+4+3+1, 30+27+21+19+6+5+1, 30+27+21+19+6+5+2+1, 30+27+21+19+6+5+3+1, 30+28+27+19+1, 30+28+27+19+3+1, 30+28+27+19+5+1, 30+28+27+19+5+2+1, 30+28+27+19+5+3+1, 30+28+27+19+6+1, 30+28+27+19+6+2+1, 30+28+27+19+6+3+1, 30+28+27+19+6+4+1, 30+28+27+19+6+4+2+1, 30+28+27+19+6+4+3+1, 30+28+27+19+6+5+1, 30+28+27+19+6+5+2+1, 30+28+27+19+6+5+3+1, 30+28+27+20+19+1, 30+28+27+20+19+3+1, 30+28+27+20+19+5+1, 30+28+27+20+19+5+2+1, 30+28+27+20+19+5+3+1, 30+28+27+20+19+6+1, 30+28+27+20+19+6+2+1, 30+28+27+20+19+6+3+1, 30+28+27+20+19+6+4+1, 30+28+27+20+19+6+4+2+1, 30+28+27+20+19+6+4+3+1, 30+28+27+20+19+6+5+1, 30+28+27+20+19+6+5+2+1, 30+28+27+20+19+6+5+3+1, 30+28+27+21+19+1, 30+28+27+21+19+3+1, 30+28+27+21+19+5+1, 30+28+27+21+19+5+2+1, 30+28+27+21+19+5+3+1, 30+28+27+21+19+6+1, 30+28+27+21+19+6+2+1, 30+28+27+21+19+6+3+1, 30+28+27+21+19+6+4+1, 30+28+27+21+19+6+4+2+1, 30+28+27+21+19+6+4+7+1, 30+28+27+21+19+6+4+3+1, 30+28+27+21+19+6+5+1, 30+28+27+21+19+6+5+2+1, 30+28+27+21+19+6+5+3+1, 30+29+27+19+1, 30+29+27+19+3+1, 30+29+27+19+5+1, 30+29+27+19+5+2+1, 30+29+27+19+5+3+1, 30+29+27+19+6+1, 30+29+27+19+6+2+1, 30+29+27+19+6+3+1, 30+29+27+19+6+4+1, 30+29+27+19+6+4+2+1, 30+29+27+19+6+4+3+1, 30+29+27+19+6+5+1, 30+29+27+19+6+5+2+1, 30+29+27+19+6+5+3+1, 30+29+27+20+19+1, 30+29+27+20+19+3+1, 30+29+27+20+19+5+1, 30+29+27+20+19+5+2+1, 30+29+27+20+19+5+3+1, 30+29+27+20+19+6+1, 30+29+27+20+19+6+2+1, 30+29+27+20+19+6+3+1, 30+29+27+20+19+6+4+1, 30+29+27+20+19+6+4+2+1, 30+29+27+20+19+6+4+3+1, 30+29+27+20+19+6+5+1, 30+29+27+20+19+6+5+2+1, 30+29+27+20+19+6+5+3+1, 30+29+27+21+19+1, 30+29+27+21+19+3+1, 30+29+27+21+19+5+1, 30+29+27+21+19+5+2+1, 30+29+27+21+19+5+3+1, 30+29+27+21+19+6+1, 30+29+27+21+19+6+2+1, 30+29+27+21+19+6+3+1, 30+29+27+21+19+6+4+1, 30+29+27+21+19+6+4+2+1, 30+29+27+21+19+6+4+3+1, 30+29+27+21+19+6+5+1, 30+29+27+21+19+6+5+2+1, 30+29+27+21+19+6+5+3+1, 30+29+28+27+19+1, 30+29+28+27+19+3+1, 30+29+28+27+19+5+1, 30+29+28+27+19+5+2+1, 30+29+28+27+19+5+3+1, 30+29+28+27+19+6+1, 30+29+28+27+19+6+2+1, 30+29+28+27+19+6+3+1, 30+29+28+27+19+6+4+1, 30+29+28+27+19+6+4+2+1, 30+29+28+27+19+6+4+3+1, 30+29+28+27+19+6+5+1, 30+29+28+27+19+6+5+2+1, 30+29+28+27+19+6+5+3+1, 30+29+28+27+20+19+1, 30+29+28+27+20+19+3+1, 30+29+28+27+20+19+5+1, 30+29+28+27+20+19+5+2+1, 30+29+28+27+20+19+5+3+1, 30+29+28+27+20+19+6+1, 30+29+28+27+20+19+6+2+1, 30+29+28+27+20+19+6+3+1, 30+29+28+27+20+19+6+4+1, 30+29+28+27+20+19+6+4+2+1, 30+29+28+27+20+19+6+4+3+1, 30+29+28+27+20+19+6+5+1, 30+29+28+27+20+19+6+5+2+1, 30+29+28+27+20+19+6+5+3+1, 30+29+28+27+21+19+1, 30+29+28+27+21+19+3+1, 30+29+28+27+21+19+5+1, 30+29+28+27+21+19+5+2+1, 30+29+28+27+21+19+5+3+1, 30+29+28+27+21+19+6+1, 30+29+28+27+21+19+6+2+1, 30+29+28+27+21+19+6+3+1, 30+29+28+27+21+19+6+4+1, 30+29+28+27+21+19+6+4+2+1, 30+29+28+27+21+19+6+4+3+1, 30+29+28+27+21+19+6+5+1, 30+29+28+27+21+19+6+5+2+1, 30+29+28+27+21+19+6+5+3+1, 31+1, 31+2+1, 31+3+1, 31+4+1, 31+4+2+1, 31+4+3+1, 31+5+1, 31+5+2+1, 31+5+3+1, 31+6+1, 31+6+2+1, 31+6+3+1, 31+6+4+1, 31+6+4+2+1, 31+6+4+3+1, 31+6+5+1, 31+6+5+2+1, 31+6+5+3+1, 31+7+6+1, 31+7+6+2+1, 31+7+6+3+1, 31+7+6+4+1, 31+7+6+4+2+1, 31+7+6+4+3+1, 31+7+6+5+1, 31+7+6+5+2+1, 31+7+6+5+3+1, 31+8+6+1, 31+8+6+2+1, 31+8+6+3+1, 31+8+6+4+1, 31+8+6+4+2+1, 31+8+6+4+3+1, 31+8+6+5+1, 31+8+6+5+2+1, 31+8+6+5+3+1, 31+9+1, 31+9+3+1, 31+9+5+1, 31+9+5+2+1, 31+9+5+3+1, 31+9+6+1, 31+9+6+2+1, 31+9+6+3+1, 31+9+6+4+1, 31+9+6+4+2+1, 31×9+6+4+3+1, 31+9+6+5+1, 31+9+6+5+2+1, 31+9+6+5+3+1, 31+10+1, 31+10+3+1, 31+10+5+1, 31+10+5+2+1, 31+10+

5+3+1, 31+10+6+1, 31+10+6+2+1, 31+10+6+3+1, 31+10+6+4+1, 31+10+6+4+2+1, 31+10+6+4+3+1, 31+10+6+5+1, 31+10+6+5+2+1, 31+10+6+5+3+1, 31+11+9+1, 31+11+9+3+1, 31+11+9+5+1, 31+11+9+5+2+1, 31+11+9+5+3+1, 31+11+9+6+1, 31+11+9+6+2+1, 31+11+9+6+3+1, 31+11+9+6+4+1, 31+11+9+6+4+2+1, 31+11+9+6+4+3+1, 31+11+9+6+5+1, 31+11+9+6+5+2+1, 31+11+9+6+5+3+1, 31+11+10+1, 31+11+10+3+1, 31+11+10+5+1, 31+11+10+5+2+1, 31+11+10+5+3+1, 31+11+10+6+1, 31+11+10+6+2+1, 31+11+10+6+3+1, 31+11+10+6+4+1, 31+11+10+6+4+2+1, 31+11+10+6+4+3+1, 31+11+10+6+5+1, 31+11+10+6+5+2+1, 31+11+10+6+5+3+1, 31+12+9+1, 31+12+9+3+1, 31+12+9+5+1, 31+12+9+5+2+1, 31+12+9+5+3+1, 31+12+9+6+1, 31+12+9+6+2+1, 31+12+9+6+3+1, 31+12+9+6+4+1, 31+12+9+6+4+2+1, 31+12+9+6+4+3+1, 31+12+9+6+5+1, 31+12+9+6+5+2+1, 31+12+9+6+5+3+1, 31+12+10+1, 31+12+10+3+1, 31+12+10+5+1, 31+12+10+5+2+1, 31+12+10+5+3+1, 31+12+10+6+1, 31+12+10+6+2+1, 31+12+10+6+3+1, 31+12+10+6+4+1, 31+12+10+6+4+2+1, 31+12+10+6+4+3+1, 31+12+10+6+5+1, 31+12+10+6+5+2+1, 31+12+10+6+5+3+1, 31+13+1, 31+13+3+1, 31+13+5+1, 31+13+5+2+1, 31+13+5+3+1, 31+13+6+1, 31+13+6+2+1, 31+13+6+3+1, 31+13+6+4+1, 31+13+6+4+2+1, 31+13+6+4+3+1, 31+13+6+5+1, 31+13+6+5+2+1, 31+13+6+5+3+1, 31+14+1, 31+14+3+1, 31+14+5+1, 31+14+5+2+1, 31+14+5+3+1, 31+14+6+1, 31+14+6+2+1, 31+14+6+3+1, 31+14+6+4+1, 31+14+6+4+2+1, 31+14+6+4+3+1, 31+14+6+5+1, 31+14+6+5+2+1, 31+14+6+5+3+1, 31+15+14+1, 31+15+14+3+1, 31+15+14+5+1, 31+15+14+5+2+1, 31+15+14+5+3+1, 31+15+14+6+1, 31+15+14+6+2+1, 31+15+14+6+3+1, 31+15+14+6+4+1, 31+15+14+6+4+2+1, 31+15+14+6+4+3+1, 31+15+14+6+5+1, 31+15+14+6+5+2+1, 31+15+14+6+5+3+1, 32+31+1, 32+31+2+1, 32+31+3+1, 32+31+4+1, 32+31+4+2+1, 32+31+4+3+1, 32+31+5+1, 32+31+5+2+1, 32+31+5+3+1, 32+31+6+1, 32+31+6+2+1, 32+31+6+3+1, 32+31+6+4+1, 32+31+6+4+2+1, 32+31+6+4+3+1, 32+31+6+5+1, 32+31+6+5+2+1, 32+31+6+5+3+1, 32+31+7+6+1, 32+31+7+6+2+1, 32+31+7+6+3+1, 32+31+7+6+4+1, 32+31+7+6+4+2+1, 32+31+7+6+4+3+1, 32+31+7+6+5+1, 32+31+7+6+5+2+1, 32+31+7+6+5+3+1, 32+31+8+6+1, 32+31+8+6+2+1, 32+31+8+6+3+1, 32+31+8+6+4+1, 32+31+8+6+4+2+1, 32+31+8+6+4+3+1, 32+31+8+6+5+1, 32+31+8+6+5+2+1, 32+31+8+6+5+3+1, 32+31+9+1, 32+31+9+3+1, 32+31+9+5+1, 32+31+9+5+2+1, 32+31+9+5+3+1, 32+31+9+6+1, 32+31+9+6+2+1, 32+31+9+6+3+1, 32+31+9+6+4+1, 32+31+9+6+4+2+1, 32+31+9+6+4+3+1, 32+31+9+6+5+1, 32+31+9+6=5+2+1, 32+31+9+6+5+3+1, 32+31+10+1, 32+31+10+3+1, 32+31+10+5+1, 32+31+10+5+2+1, 32+31+10+5+3+1, 32+31+10+6+1, 32+31+10+6+2+1, 32+31+10+6+3+1, 32+31+10+6+4+1, 32+31+10+6+4+2+1, 32+31+10+6+4+3+1, 32+31+10+6+5+1, 32+31+10+6+5+2+1, 32+31+10+6+5+3+1, 32+31+11+9+1, 32+31+11+9+3+1, 32+31+11+9+5+1, 32+31+11+9+5+2+1, 32+31+11+9+5+3+1, 32+31+11+9+6+1, 32+31+11+9+6+2+1, 32+31+11+9+6+3+1, 32+31+11+9+6+4+1, 32+31+11+9+6+4+2+1, 32+31+11+9+6+4+3+1, 32+31+11+9+6+5+1, 32+31+11+9+6+5+2+1, 32+31+11+9+6+5+3+1, 32+31+11+10+1, 32+31+11+10+3+1, 32+31+11+10+5+1, 32+31+11+10+5+2+1, 32+31+11+10+5+3+1, 32+31+11+10+6+1, 32+31+11+10+6+2+1, 32+31+11+10+6+3+1, 32+31+11+10+6+4+1, 32+31+11+10+6+4+2+1, 32+31+11+10+6+4+3+1, 32+31+11+10+6+5+1, 32+31+11+10+6+5+2+1, 32+31+11+10+6+5+3+1, 32+31+12+9+1, 32+31+12+9+3+1, 32+31+12+9+5+1, 32+31+12+9+5+2+1, 32+31+12+9+5+3+1, 32+31+12+9+6+1, 32+31+12+9+6+2+1, 32+31+12+9+6+3+1, 32+31+12+9+6+4+1, 32+31+12+9+6+4+2+1, 32+31+12+9+6+4+3+1, 32+31+12+9+6+5+1, 32+31+12+9+6+5+2+1, 32+31+12+9+6+5+3+1, 32+31+12+10+1, 32+31+12+10+3+1, 32+31+12+10+5+1, 32+31+12+10+5+2+1, 32+31+12+10+5+3+1, 32+31+12+10+6+1, 32+31+12+10+6+2+1, 32+31+12+10+6+3+1, 32+31+12+10+6+4+1, 32+31+12+10+6+4+2+1, 32+31+12+10+6+4+3+1, 32+31+12+10+6+5+1, 32+31+12+10+6+5+2+1, 32+31+12+10+6+5+3+1, 32+31+13+1, 32+31-13+3+1, 32+31+13+5+1, 32+31+13+5+2+1, 32+31+13+5+3+1, 32+31+13+6-1, 32+31+13+6+2+1, 32+31+13+6+3+1, 32+31+13+6+4+1, 32+31+13+6+4+2+1, 32+31+13+6+4+3+1, 32+31+13+6+5+1, 32+31+13+6+5+2+1, 32+31+13+6+5+3+1, 32+31+14+1, 32+31+14+3+1, 32+31+14+5+1, 32+31+14+5+2+1, 32+31+14+5+3+1, 32+31+14+6+1, 32+31+14+6+2+1, 32+31+14+6+3+1, 32+31+14+6+4+1, 32+31+14+6+4+2+1, 32+31+14+6+4+3+1, 32+31+14+6+5+1, 32+31+14+6+5+2+1, 32+31+14+6+5+3+1, 32+31+15+14+1, 32+31+15+14+3+1, 32+31+15+14+5+1, 32+31+15+14+5+2+1, 32+31+15+14+5+3+1, 32+31+15+14+6+1, 32+31+15+14+6+2+1, 32+31+15+14+6+3+1, 32+31+15+14+6+4+1, 32+31+15+14+6+4+2+1, 32+31+15+14+6+4+3+1, 32+31+15+14+6+5+1, 32+31+15+14+6+5+2+1, 32+31+15+14+6+5+3+1, 33+31+1, 33+31+2+1, 33+31+3+1, 33+31+4+1, 33+31+4+2+1, 33+31+4+3+1, 33+31+5+1, 33+31+5+2+1, 33+31+5+3+1, 33+31+6+1, 33+31+6+2+1, 33+31+6+3+1, 33+31+6+4+1, 33+31+6+4+2+1, 33+31+6+4+3+1, 33+31+6+5+1, 33+31+6+5+2+1, 33+31+6+5+3+1, 33+31+7+6+1, 33+31+7+6+2+1, 33+31+7+6+3+1, 33+31+7+6+4+1, 33+31+7+6+4+2+1, 33+31+7+6+4+3+1, 33+31+7+6+5+1, 33+31+7+6+5+2+1, 33+31+7+6+5+3+1, 33+31+8+6+1, 33+31+8+6+2+1, 33+31+8+6+3+1, 33+31+8+6+4+1, 33+31+8+6+4+2+1, 33+31+8+6+4+3+1, 33+31+8+6+5+1, 33+31+8+6+5+2+1, 33+31+8+6+5+3+1, 33+31+9+1, 33+31+9+3+1, 33+31+9+5+1, 33+31+9+5+2+1, 33+31+9+5+3+1, 33+31+9+6+1, 33+31+9+6+2+1, 33+31+9+6+3+1, 33+31+9+6+4+1, 33+31+9+6+4+2+1, 33+31+9+6+4+3+1, 33+31+9+6+5+1, 33+31+9+6+5+2+1, 33+31+9+6+5+3+1, 33+31+10+1, 33+31+10+3+1, 33+31+10+5+1, 33+31+10+5+2+1, 33+31+10+5+3+1, 33+31+10+6+1, 33+31+10+6+2+1, 33+31+10+6+3+1, 33+31+10+6+4+1, 33+31+10+6+4+2+1, 33+31+10+6+4+3+1, 33+31+10+6+5+1, 33+31+10+6+5+2+1, 33+31+10+6+5+3+1, 33+31+11+9+1, 33+31+11+9+3+1, 33+31+11+9+5+1, 33+31+11+9+5+2+1, 33+31+11+9+5+3+1, 33+31+11+9+6+1, 33+31+11+9+6+2+1, 33+31+11+9+6+3+1, 33+31+11+9+6+4+1, 33+31+11+9+6+4+2+1, 33+31+11+9+6+4+3+1, 33+11+11+9+6+5+1, 33+31+11+9+6+5+2+1, 33+31+11+9+6+5+3+1, 33+31+11+10+1, 33+31+11+10+3+1, 33+31+11+10+5+1, 33+31+11+10+5+2+1, 33+31+11+10+5+3+1, 33+31+11+10+6+1, 33+31+11+10+6+2+1, 33+31+11+10+6+3+1, 33+31+11+10+6+4+1, 33+31+11+10+6+4+2+1, 33+31+11+10+6+4+3+1, 33+31+11+10+6+5+1, 33+31+11+10+6+5+2+1, 33+31+11+10+6+5+3+1, 33+31+12+9+1, 33+31+12+9+3+1, 33+31+12+9+5+1, 33+31+12+9+5+2+1, 33+31+12+9+5+3+1, 33+31+12+9+6+1, 33+31+12+9+6+2+1, 33+31+12+9+6+3+1, 33+31+12+9+6+4+1, 33+31+12+9+6+4+2+1, 33+31+12+9+6+4+3+1, 33+31+12+9+6+5+1, 33+31+12+9+6+5+2+1, 33+31+12+9+6+5+3+1, 33+31+12+10+1, 33+31+12+10+3+1, 33+31+12+10+5+1, 33+31+12+10+5+2+1, 33+31+12+10+5+3+1, 33+31+12+10+6+1 33+31+12+10+6+2+1 33+31+12+10+6+3+1, 33+31+12+10+6+4+1, 33+31+12+10+6+4+2+1, 33+31+12+10+6+4+3+1, 33+31+

12+10+6+5+1, 33+31+12+10+6+5+2+1, 33+31+12+10+6+ 5+3+1, 33+31+13+1, 33+31+13+3+1, 33+31+13+5+1, 33+31+13+5+2+1, 33+31+13+5+3+1, 33+31+13+6+1, 33+31+13+6+2+1, 33+31+13+6+3+1, 33+31+13+6+4+1, 33+31+13+6+4+2+1, 33+31+13+6+4+3+1, 33+31+13+6+5+1, 33+31+13+6+5+2+1, 33+31+13+6+5+3+1, 33+31+14+1, 33+31+14+3+1, 33+31+ 14+5+1, 33+31+14+5+2+1, 33+31+14+5+3+1, 33+31+1.4+ 6+1, 33+31+14+6+2+1, 33+31+14+6+3+1, 33+31+14+6+4+ 1, 33+31+14+6+4+2+1, 33+31+14+6+4+3+1, 33+31+14+6+ 5+1, 33+30+14+6+5+2+1, 33+31+14+6+5+3+1, 33+31+15+ 14+1, 33+31+15+14+3+1, 33+31+15+14+5+1, 33+31+15+ 14+5+2+1, 33+31+15+14+5+3+1, 33+31+15+14+6+1, 33+31+15+14+6+2+1, 33+31+15+14+6+3+1, 33+31+15+14+6+4+1, 33+31+15+14+6+4+2+1, 33+31+15+14+6+4+3+1, 33+31+15+14+6+5+1, 33+31+15+14+6+5+2+1, 33+31+15+14+6+5+3+1, 34, 35+34 and 36+34.

In the list above, the numbers refer to the embodiments according to their numbering provided hereinabove whereas "+" indicates the dependency from another embodiment. The different individualised embodiments are separated by commas. In other words, "5+3+1" for example refers to embodiment 5) depending on embodiment 3), depending on embodiment 1), i.e. embodiment "5+3+1" corresponds to embodiment 1) further limited by the features of embodiments 3) and 5). Likewise, "11+9+5+1" refers to embodiment 11) depending mutatis mutandis on embodiments 9) and 5), depending on embodiment 1), i.e. embodiment "11+9+5+1" corresponds to embodiment 1) further limited by the features of embodiment 5), further limited by the features of embodiments 9) and 11).

ABBREVIATIONS AND TERMS USED IN THIS TEXT

Abbreviations:
The following abbreviations are used throughout the specification and the examples:
Ac acetyl
aq. aqueous
CHex cyclohexane
conc. concentrated
DCM dichloromethane
DMAC dimethylacetamide
DME 1,2-dimethoxyethane
DMF dimethylformamide
DMSO dimethylsulfoxide
d6-DMSO perdeuterated dimethylsulfoxide
EA ethyl acetate
eq. equivalent(s)
Hept heptane
Hex hexane
IPC In Process Control
iPrOAc isopropyl acetate
LC-MS liquid chromatography-mass spectroscopy
MS mass spectroscopy
MeCHex methylcyclohexane
MeCN acetonitrile
MeOH methanol
NMP N-methylpyrrolidone
% aa percent determined by area ratio
rt room temperature
TBME tent-butyl methyl ether
TFA trifluoroacetic acid
THF tetrahydrofurane
$t_R$ retention time

DEFINITIONS OF PARTICULAR TERMS USED IN THIS TEXT

The following paragraphs provide definitions of the various chemical moieties for the compounds according to the invention as well as other particular terms used in this text and are intended to apply uniformly throughout the specification and claims, unless an otherwise expressly set out definition provides a broader or narrower definition:

The expression "sulfuric acid" refers to a mixture of $H_2SO_4$ and water, which can also contain $SO_3$. Preferably, sulfuric acid will be sulfuric acid having a concentration of at least 95% in weight, and in particular sulfuric acid having a concentration of at least 98% in weight.

The expression "inert gas" refers to a gas selected from nitrogen, helium and argon (nitrogen being preferred).

The expression "inert gas mixture" refers to a mixture of two or more gases selected from inert gases as defined before.

The expression "polar aprotic solvent" refers to a solvent which does not display hydrogen bonding, does not have an acidic hydrogen but is able to stabilise ions. Representative examples of polar aprotic solvents include DCM, MeCN, EA, iPrOAc, THF, 2-methyl-tetrahydrofurane, DMAC, DME, DMF, DMSO, dioxane, diethyl ether, NMP, TBME or cyclopentyl methyl ether.

The expression "polar aprotic mixture of solvents" refers to a mixture of solvents which includes at least one polar aprotic solvent as previously defined and at least another aprotic solvent (which may be polar or apolar). Representative examples of polar aprotic mixtures of solvents include, but are not limited to: a mixture of two solvents selected from the group consisting of DCM, MeCN, EA, iPrOAc, THF, 2-methyl-tetrahydrofurane, DMAC, DME, DMF, DMSO, dioxane, diethyl ether, NMP, TBME and cyclopentyl methyl ether; a mixture of toluene with one or more of DCM, MeCN, EA, iPrOAc, THF, 2-methyl-tetrahydrofurane, DMAC, DME, DMF, DMSO, dioxane, diethyl ether, NMP, TBME or cyclopentyl methyl ether; a mixture of Hex with one or more of DCM, MeCN, EA, iPrOAc, THF, 2-methyl-tetrahydrofurane, DMAC, DME, DMF, DMSO, dioxane, diethyl ether, TBME or cyclopentyl methyl ether; a mixture of Hept with one or more of DCM, MeCN, EA, iPrOAc, THF, 2-methyl-tetrahydrofurane, DMAC, DME, DMF, DMSO, dioxane, diethyl ether, TBME or cyclopentyl methyl ether; and a mixture of toluene with Hex, CHex, MeCHex or Hept and one or more of DCM, MeCN, EA, iPrOAc, THF, 2-methyl-tetrahydrofurane, DMAC, DME, DMF, DMSO, dioxane, diethyl ether, TBME or cyclopentyl methyl ether.

The expression "room temperature" as used herein refers to a temperature of from 20 to 30° C., and preferably 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

Particular embodiments of the invention are described in the following Examples, which serve to illustrate the invention in more detail without limiting its scope in any way.

EXAMPLES

All temperatures given are external temperatures and are stated in ° C. Compounds were characterized by $^1$H-NMR (400 MHz) or $^{13}$C-NMR (100 MHz) (Bruker; chemical shifts δ are given in ppm relative to the solvent used; multiplicities: s=singlet, d=doublet, t=triplet; p=pentuplet, hex=hextet, hept=heptet, m=multiplet, br.=broad, coupling constants are given in Hz); by LC-MS (Agilent MS detector G1956B with Agilent 1200 Binary Pump and DAD); or by HPLC. $t_R$ is given in minutes.

Parameters of the HPLC Method:
Injection volume: 2 μL
Column: Hypersil BDS $C_{18}$, 125 mm×4 mm×5 μm
Eluents: Eluent A: water/MeCN 99/1+0.1% TFA
Eluent B: water/MeCN 40/60+0.1% TFA
Gradient: from eluent A to eluent B in 6 min, then 2 min pure MeCN
Flow rate 1 mL/min
UV detector wavelength 220 nm

Example 1

8-bromo-7-fluoro-2-methoxy-1,5-naphthyridine 1.i. 3-fluoro-6-methoxy-1,5-naphthyridin-4-ol Variant 1 (Fluorine Not Going Through a Frit):

Concentrated sulfuric acid (100 mL) was charged in a 500 mL fluorination apparatus. 6-methoxy-1,5-naphthyridine-4-ol (1 g, 1 eq.; preparation described e.g. at Example 18, step (b) of WO 02/08224) was added. The suspension was magnetically stirred. After 10 min a clear brown solution was obtained. The solution was cooled to 0° C. using an ice bath. Once 0° C. was reached, 10% $F_2$ in $N_2$ was bubbled through the reaction mixture at a rate of about 20 L/h using a teflon tube at the lowest point of the apparatus. IPC (by LC-MS at 220 nm) showed no conversion to the product after 45 min. The solution was heated to 20° C. using a water bath. 10% $F_2$ in $N_2$ was bubbled through the reaction mixture at a rate of about 20 L/h. IPC showed 1% conversion to the product after 1 h. The solution was heated to 40° C. 10% $F_2$ in $N_2$ was bubbled through the reaction mixture at a rate of about 20 L/h. IPC showed 5% conversion to the product after 30 min. The solution was heated to 80° C. 10% $F_2$ in $N_2$ was bubbled through the reaction mixture at a rate of about 20 L/h. IPC showed 11% conversion to the product after 40 min. The reaction mixture was slowly added to crushed ice and diluted with water. A NaOH solution along with NaOH pellets were added at 10° C. to 50° C. until the pH reached 8.0. The resulting aq. phase (800 mL) was extracted with DCM (800 mL) and the layers were separated. LCMS at 254 nm of the org. phase revealed 18% of the desired product along with 63% of starting material. The org. phase was evaporated and the crude was purified by column chromatography (10% MeOH in DCM) resulting in a white solid (0.05 g, 4.5% yield).

HPLC: $t_R$=3.2 min; purity: 81% aa (no starting material).
Flow Injection Mass Spectroscopy, electrospray ionization: $[M+1]^+$=195.

Variant 2 (Fluorine Not Going Through a Frit, Higher Temperature):

Concentrated sulfuric acid (100 mL) was charged in a 500 mL fluorination apparatus. 6-methoxy-1,5-naphthyridine-4-ol (1 g, 1 eq.) was added. The suspension was magnetically stirred. After 10 min a clear brown solution was obtained. The solution was heated to 80° C. using an oil bath. Once 80° C. were reached, 10% $F_2$ in $N_2$ was bubbled through the reaction mixture at a rate of about 20 L/h using a teflon tube at the lowest point of the apparatus. IPC (by LC-MS at 220 nm) showed 11% conversion to the product after 4 h. The solution was heated to 95° C. 10% $F_2$ in $N_2$ was bubbled through the reaction mixture at a rate of about 20 L/h. IPC showed 30% conversion to the product after 6 h (HPLC ratio of starting material/desired product/by-products is 70/30/0). The solution was heated to 125° C. 10% $F_2$ in $N_2$ was bubbled through the reaction mixture at a rate of about 20 L/h. IPC showed a ratio of starting material/desired product/byproducts of 40/18/42 after 2 h.

Variant 3 (Fluorine Going Through a Frit (10 μm Pore Size)):

Concentrated sulfuric acid (100 mL) was charged in a 500 mL fluorination apparatus. 6-methoxy-1,5-naphthyridine-4-ol (1 g, 1 eq.) was added. The suspension was magnetically stirred. After 10 min a clear brown solution was obtained. The solution was heated to 80° C. using an oil bath. Once 80° C. were reached, 10% $F_2$ in $N_2$ was bubbled through the reaction mixture at a rate of about 20 L/h using a teflon tube with teflon frit (10 μm pore size) at the lowest point of the apparatus. IPC showed 90% conversion to the product after 2 h. The reaction mixture was slowly added to crushed ice (100 g) while temperature rised to 60° C. With cooling, a 28% aq. ammonia solution (340 mL) was slowly added at 10-25° C. The final pH of the suspension was 7.6. The mixture was stirred for 30 min at rt. The product was filtered and dried at 70° C. in a vacuum oven for 16 h to afford the desired compound as a grey solid (0.5 g, 45% yield).

HPLC: $t_R$=3.2 min; purity: 92% aa.
Flow Injection Mass Spectroscopy, electrospray ionization: $[M+1]^+$=195.

Variants 4 to 13 (Variation of the Solvent):

Further experiments have been performed using the protocol described for Variant 3, with however variations regarding the reaction solvent S, the reaction mixture temperature T and/or the reaction duration D, and the performance of the reaction in an autoclave instead of in a fluorination apparatus for Variant 13. The results thus obtained are summarised in the table hereafter (SM/DP/BP denoting the ratio starting material/desired product/by-product as measured by HPLC) have been obtained:

| Variant No. | S | T (° C.) | D (h) | SM/DP/BP |
| --- | --- | --- | --- | --- |
| 4 | conc. $H_2SO_4$ | 80-95 | 10 | 70/30/0 |
| 5 | HCOOH | 20 | 1.5 | 44/3/53 |
| 6 | HCOOH | 60 | 3 | 20/3/77 |
| 7 | AcOH | 20 | 1 | 0/0/100 |
| 8 | $CHCl_3$ | 60 | 7 | 93/2/5 |
| 9 | DMF | 20 | 2 | 45/0/55 |
| 10 | MeCN | 0 | 1 | 85/0/15 |
| 11 | MeCN | 20 | 2 | 0/0/100 |
| 12 | 10% aq. $H_2SO_4$ | 20 | 1 | 43/6/51 |
| 13 | anhydrous HF | 60 | 2 | 68/24/8 |

Variant 14 (Fluorine Going Through a Frit (20 μm Pore Size)):

Concentrated sulfuric acid (500 mL) was charged in a 1 L fluorination apparatus. 6-methoxy-1,5-naphthyridin-4-ol (50 g, 1 eq.) was added, followed by silica gel (10 g). The suspension was magnetically stirred. After 5 min a clear brown solution was obtained. The solution was heated to 80° C. using an oil bath. Once 80° C. was reached, 10% $F_2$ in $N_2$ was bubbled through the reaction mixture at a rate of about 30 L/h using a teflon tube with glass frit (20 μm pore size) at the lowest point of the apparatus (NB: the gas flow rate was however adjusted at 30-60 L/h throughout the reaction to control foaming). In Process Control (IPC by LCMS) showed 93% conversion to the product after 27 h. The reaction mixture was slowly added to crushed ice (400 g), keeping the temperature below 20° C. This mixture was slowly added to a pre-cooled (about 5° C.) 28% aq. ammonia solution (1.65 L) at 0-20° C. The final pH of the suspension was 7.4. The mixture was stirred for 2 h at rt. The product was filtered and dried at 70° C. in a vacuum oven for 16 h to afford the desired compound as a grey solid (22.5 g; 41% yield).

HPLC: $t_R$=3.2 min; purity: 94% a/a.

LC-MS: $[M+1]^-$=195.

1.ii. 8-bromo-7-fluoro-2-methoxy-1,5-naphthyridine:

To a warmed (about 50° C.) mixture of intermediate 1.i (1.50 g; 1 eq.) in DMF (10 mL) was added tribromophosphine (0.82 mL; 1.1 eq.). The mixture was stirred at 70° C. for 1 h. After cooling to rt, the reaction mixture was diluted with water (500 mL), and 6N NaOH (1.3 mL) was added. The solid was filtered off and thoroughly washed with water. The resulting solid was taken up in EA and the solution was filtered through a pad of silica to afford the desired compound as a light beige solid (2.0 g; quantitative yield).

$^1$H NMR (d6-DMSO) δ: 8.86 (s, 1H), 8.34 (d, J=9.0 Hz, 1H), 7.31 (d, J=9.1 Hz, 1H), 4.08 (m, 3H).

Example 2

8-chloro-7-fluoro-2-methoxy-1,5-naphthyridine

POCl$_3$ (1.6 g, 2 eq.) was slowly added to a suspension of intermediate 1.i (1 g, 5.2 mmol) in DMF (6 mL) at 5° C. The suspension turned into a black solution. The temperature was raised to 25° C. and the solution was stirred for 5 min. The reaction mixture was added to water (25 mL) at 5° C. To the mixture was added iPrOAc (25 mL) and the pH was adjusted to 7 with 2N NaOH (20 mL). The layers were separated and the org. layer was washed with water (2×25 mL). The org. layer was dried over MgSO$_4$ (5 g), filtered and evaporated to dryness under reduced pressure at 60° C. to yield the desired compound as a brown solid (0.78 g, 71% yield).

HPLC (LC-MS: column: Kinetex C$_{18}$, 50 mm×2.1 mm×2.6 μm, eluent: MeCN (with 0.012% TFA)/water (with 0.08% TFA), gradient: 95% MeCN during 2.8 min, then to 5% MeCN in 3.0 min, flow 1 mL/min, 220 nm): $t_R$=1.5 min; $[M+1]^+$=213; purity: 97.6% a/a.

$^1$H NMR (CDCl$_3$) δ: 8.71 (s, 1H), 8.23 (d, J=9.1 Hz, 1H), 7.16 (d, J=9.1 Hz, 1H), 4.18 (s, 3H).

The invention claimed is:

1. A method for manufacturing a compound of formula I-2

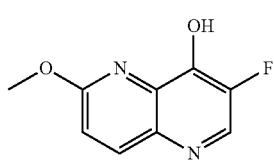

comprising reacting a compound of formula (I-1)

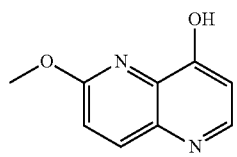

with fluorine gas in the presence of sulfuric acid at a temperature from 20° C. to 100° C.

2. The method according to claim 1, wherein the reacting is performed in sulfuric acid having a concentration of at least 60% in weight.

3. The method according to claim 1, wherein the reacting is performed in sulfuric acid having a concentration of at least 95% in weight.

4. The method according to claim 1, wherein the reacting is performed using fluorine filtered through a frit filter.

5. The method according claim 4, wherein the frit filter has a pore size ranging from 10 to 25 μm.

6. A method for manufacturing a compound of formula I-3

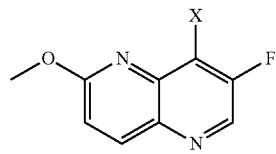

wherein X is Br or Cl, comprising the manufacturing method according to claim 1.

7. The method according to claim 6, wherein X is Br.

8. The method according to claim 6, wherein X is Cl.

9. A method for manufacturing the compound of formula I-3

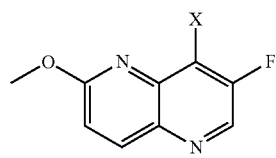

wherein X is Br or GI Cl, comprising:
  a) performing the process according to claim 1; and
  b) reacting the compound of formula I-2 obtained in step a) with tribromophosphine in a polar aprotic solvent or a polar aprotic mixture of solvents, or reacting the compound of formula 1-2 obtained at step a) with phosphoryl trichloride, thus obtaining the compound of formula I-3.

10. The method according to claim 9, wherein the compound of formula I-2 obtained at step a) is reacted with tribromophosphine.

11. The method according to claim 9, wherein the compound of formula I-2 obtained at step a) is reacted with phosphoryl trichloride.

12. A method for manufacturing the compound of formula I-4

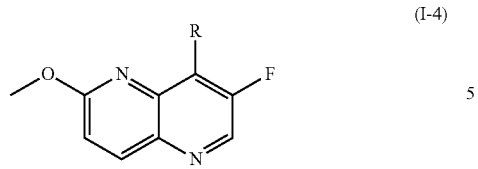
(I-4)
wherein R is H or methyl, comprising the manufacturing method according to claim 1.
13. The method according to claim 12, wherein R is H.
14. The method according to claim 12, wherein R is methyl.
15. The method according to claim 9, wherein the compound of formula I-2 is reacted with phosphoryl trichloride in a polar aprotic solvent or a polar aprotic mixture of solvents.
* * * * *